United States Patent
Zhang et al.

(10) Patent No.: US 7,923,683 B2
(45) Date of Patent: Apr. 12, 2011

(54) METHOD FOR TREATMENT OF SAMPLES FOR TRANSMISSION ELECTRON MICROSCOPES

(75) Inventors: Qi Hua Zhang, Shanghai (CN); Chorng Shyr Niou, Shanghai (CN); Pan Liu, Shanghai (CN); Ming Li, Shanghai (CN)

(73) Assignee: Semiconductor Manufacturing International (Shanghai) Corporation, Shanghai (CN)

( * ) Notice: Subject to any disclaimer, the term of this patent is extended or adjusted under 35 U.S.C. 154(b) by 138 days.

(21) Appl. No.: 12/258,965

(22) Filed: Oct. 27, 2008

(65) Prior Publication Data

US 2010/0006754 A1 Jan. 14, 2010

(30) Foreign Application Priority Data

Jul. 8, 2008 (CN) .......................... 2008 1 0040369

(51) Int. Cl.
*G06F 17/50* (2006.01)
*G06K 9/00* (2006.01)
(52) U.S. Cl. ........ 250/310; 250/306; 250/307; 250/311; 250/492.2; 250/492.3
(58) Field of Classification Search .................. 250/306, 250/307, 309–311, 492.1, 492.2, 492.3
See application file for complete search history.

(56) References Cited

U.S. PATENT DOCUMENTS

| | | | |
|---|---|---|---|
| 6,753,253 B1 * | 6/2004 | Takahashi et al. | 438/676 |
| 7,064,445 B2 * | 6/2006 | Yu et al. | 257/778 |
| 7,327,444 B2 * | 2/2008 | Naka et al. | 356/73 |
| 7,340,703 B2 * | 3/2008 | Hegazy et al. | 716/5 |
| 7,769,214 B2 * | 8/2010 | Wehrli et al. | 382/128 |
| 7,772,554 B2 * | 8/2010 | Sugiyama et al. | 250/310 |
| 2004/0114789 A1 * | 6/2004 | Saha et al. | 382/128 |
| 2004/0161865 A1 * | 8/2004 | Yu et al. | 438/14 |
| 2004/0173794 A1 * | 9/2004 | Yu et al. | 257/48 |
| 2006/0038980 A1 * | 2/2006 | Naka et al. | 356/73 |
| 2008/0295965 A1 * | 12/2008 | Nogami et al. | 156/345.51 |

\* cited by examiner

*Primary Examiner* — Bernard E Souw
(74) *Attorney, Agent, or Firm* — Townsend and Townsend and Crew LLP

(57) ABSTRACT

A method for analyzing a sample for the manufacture of integrated circuits, e.g., dynamic random access memory devices, commonly called DRAMS. The method also provides an integrated chip including a thickness, a width, and a length. In a specific embodiment, the integrated chip has at least one elongated structure through a portion of the thickness, while being normal to the width and the length. In a specific embodiment, the elongated structure has a structure width and a structure length that extends through a vertical portion of the thickness. The method includes removing a slice of the integrated chip from a portion of the thickness in a directional manner normal to the structure length. In a specific embodiment, the slice is provided through an entirety of the one elongated structure along the structure length to cause a portion of a thickness of the slice providing the elongated structure to be of a substantially uniform sample thickness. The method also includes capturing one or more images through a portion of the slice using a transmission electron microscope.

20 Claims, 7 Drawing Sheets

METHOD FOR TREATMENT OF SAMPLES FOR TRANSMISSION ELECTRON MICROSCOPES

CROSS-REFERENCE TO RELATED APPLICATIONS

This application claims priority to Chinese Patent Application No. 200810040369.X, filed Jul. 8, 2008, commonly assigned, and incorporated herein by reference for all purposes.

BACKGROUND OF THE INVENTION

The present invention is directed to integrated circuits and their processing for the manufacture of semiconductor devices. More particularly, the invention provides a method and device for treating samples for transmission electron microscopes in the manufacture of integrated circuit devices, but it would be recognized that the invention has a much broader range of applicability.

Integrated circuits have evolved from a handful of interconnected devices fabricated on a single chip of silicon to millions of devices. Conventional integrated circuits provide performance and complexity far beyond what was originally imagined. In order to achieve improvements in complexity and circuit density (i.e., the number of devices capable of being packed onto a given chip area), the size of the smallest device feature, also known as the device "geometry", has become smaller with each generation of integrated circuits.

Increasing circuit density has not only improved the complexity and performance of integrated circuits but has also provided lower cost parts to the consumer. An integrated circuit or chip fabrication facility can cost hundreds of millions, or even billions, of U.S. dollars. Each fabrication facility will have a certain throughput of wafers, and each wafer will have a certain number of integrated circuits on it. Therefore, by making the individual devices of an integrated circuit smaller, more devices may be fabricated on each wafer, thus increasing the output of the fabrication facility. Making devices smaller is very challenging, as each process used in integrated fabrication has a limit. That is to say, a given process typically only works down to a certain feature size, and then either the process or the device layout needs to be changed. Additionally, as devices require faster and faster designs, process limitations exist with certain conventional processes and materials. Furthermore, certain analysis techniques often breakdown and cannot be used effectively as device sizes become smaller and smaller.

An example of an analysis process that has limitations based upon a given feature size is the use of a transmission electron microscope for analysis for integrated circuit devices and structures of the integrated circuit devices. Such TEM analysis techniques often rely upon sample preparation to make "thin" but accurate structures that can be imaged using electron sources. Such TEM sample preparations often become difficult to perform as device features become smaller and smaller. As certain device features become very small, accurate TEM images are often difficult to produce. These and other limitations of the conventional TEM analysis techniques can be found throughout the present specification and more particularly below.

From the above, it is seen that an improved technique for processing semiconductor devices is desired.

BRIEF SUMMARY OF THE INVENTION

According to the present invention, techniques for processing integrated circuits for the manufacture of semiconductor devices are provided. More particularly, the invention provides a method and device for treating samples for transmission electron microscopes in the manufacture of integrated circuit devices, but it would be recognized that the invention has a much broader range of applicability.

In a specific embodiment, the present invention provides a method for analyzing a sample for the manufacture of integrated circuits, e.g., dynamic random access memory device, commonly called, DRAMS. The method also provides an integrated chip including a thickness, a width, and a length. In a specific embodiment, the integrated chip has at least one elongated structure through a portion of the thickness, while being normal to the width and the length. In a specific embodiment, the elongated structure has a structure width and a structure length that extends through a vertical portion of the thickness. The method includes removing a slice of the integrated circuit chip from a portion of the thickness in a directional manner normal to the structure length. In a specific embodiment, the slice is provided through an entirety of the one elongated structure along the structure length to cause a portion of a thickness of the slice providing the elongated structure to be of a substantially uniform sample thickness. The method also includes capturing one or more images through a portion of the slice using a transmission electron microscope.

In an alternative specific embodiment, the present invention provides a method for analyzing a sample for the manufacture of integrated circuits. The method includes providing an integrated chip including a thickness, a width, and a length. The integrated chip has a plurality of elongated structures in a direction of the thickness, while being normal to the width and the length. Each of the elongated structures has a structure width and a structure length, which extends through a vertical portion of the thickness. The method includes removing a slice of the integrated circuit chip from a portion of the thickness in a directional manner normal to each of the elongated structures. The slice is provided through an entirety of each of the elongated structures along each of the structure lengths to cause each of the elongated structures to be of a substantially uniform sample thickness. The method includes capturing one or more images through a portion of the slice using a transmission electron microscope.

Many benefits are achieved by way of the present invention over conventional techniques. For example, the present technique provides an easy to use process that relies upon conventional technology. In some embodiments, the method provides improved resolution of samples used for TEM analysis. Additionally, the method provides a process that is compatible with conventional process technology without substantial modifications to conventional equipment and processes . . . . Preferably, the invention provides for an improved TEM sample for dynamic random access memory devices formed in an array configuration according to a specific embodiment. Depending upon the embodiment, one or more of these benefits may be achieved. These and other benefits will be described in more throughout the present specification and more particularly below.

Various additional objects, features and advantages of the present invention can be more fully appreciated with reference to the detailed description and accompanying drawings that follow.

DETAILED DESCRIPTION OF THE INVENTION

According to the present invention, techniques for processing integrated circuits for the manufacture of semiconductor devices are provided. More particularly, the invention provides a method and device for treating samples for transmission electron microscopes in the manufacture of integrated circuit devices, but it would be recognized that the invention has a much broader range of applicability.

High aspect ratio structures are often necessary components for DRAM devices. In order to achieve the large capacitance values, some special capacitor structures such as stacked capacitor or deep trench are often used in a DRAM device. In the case of a deep trench capacitor structure, the trench is usually very deep and sometimes can be up to 7 micrometers in depth while the area is only 0.1 micron by 0.2 micron. In order to inspect dielectric layer thickness on different capacitor sites of the trench structure using TEM, each of the areas of interest of the trench must often be "thin" enough for TEM observation. That is, the term "thin" refers to the ability for the TEM to generate images effectively. However, it is often difficult to prepare a TEM sample with a good overview of the deep trench from top to bottom observable in TEM using a conventional TEM sample preparation method. For example, if we use an ion milling method to form the thin sample, usually only half of the trench is thin enough for TEM observation. Further details of conventional ion milling techniques can be found throughout the present specification and more particularly below.

Figure 1:
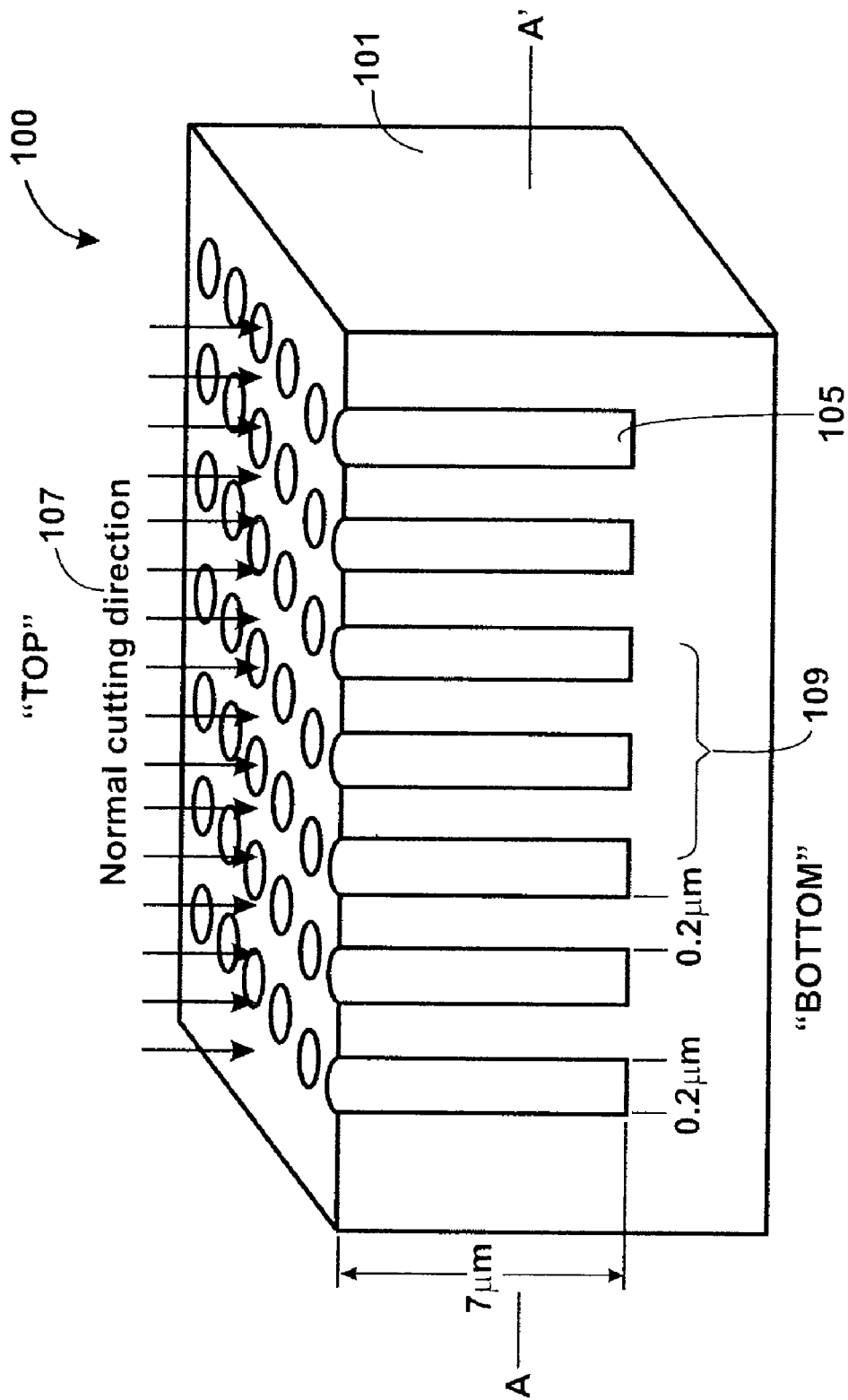
FIG. 1 is a simplified diagram illustrating a conventional method for preparing a sample for TEM analysis of a DRAM capacitor structure.

As merely an example, FIG. 1 is a simplified diagram illustrating a conventional method for preparing a sample of a DRAM capacitor structure for TEM analysis. As shown, the DRAM capacitor structure 100 includes a substrate 101, which is often single crystal silicon. The substrate has a plurality of trench structures 105 that are provided in an array configuration 109. As shown, each of the trench structures has a width of about 0.1 microns and a depth of about 7 microns to form a very large aspect ratio. It is very difficult to use a conventional focused ion beam method (i.e. cutting sample from wafer surface 107) to produce a membrane with each of the 7 micron range in vertical direction of each capacitor thin enough for TEM observation. A precise control of a ion beam tilt angle to avoid sample cutting through is often difficult using conventional focused ion beam technique.

Figure 2:
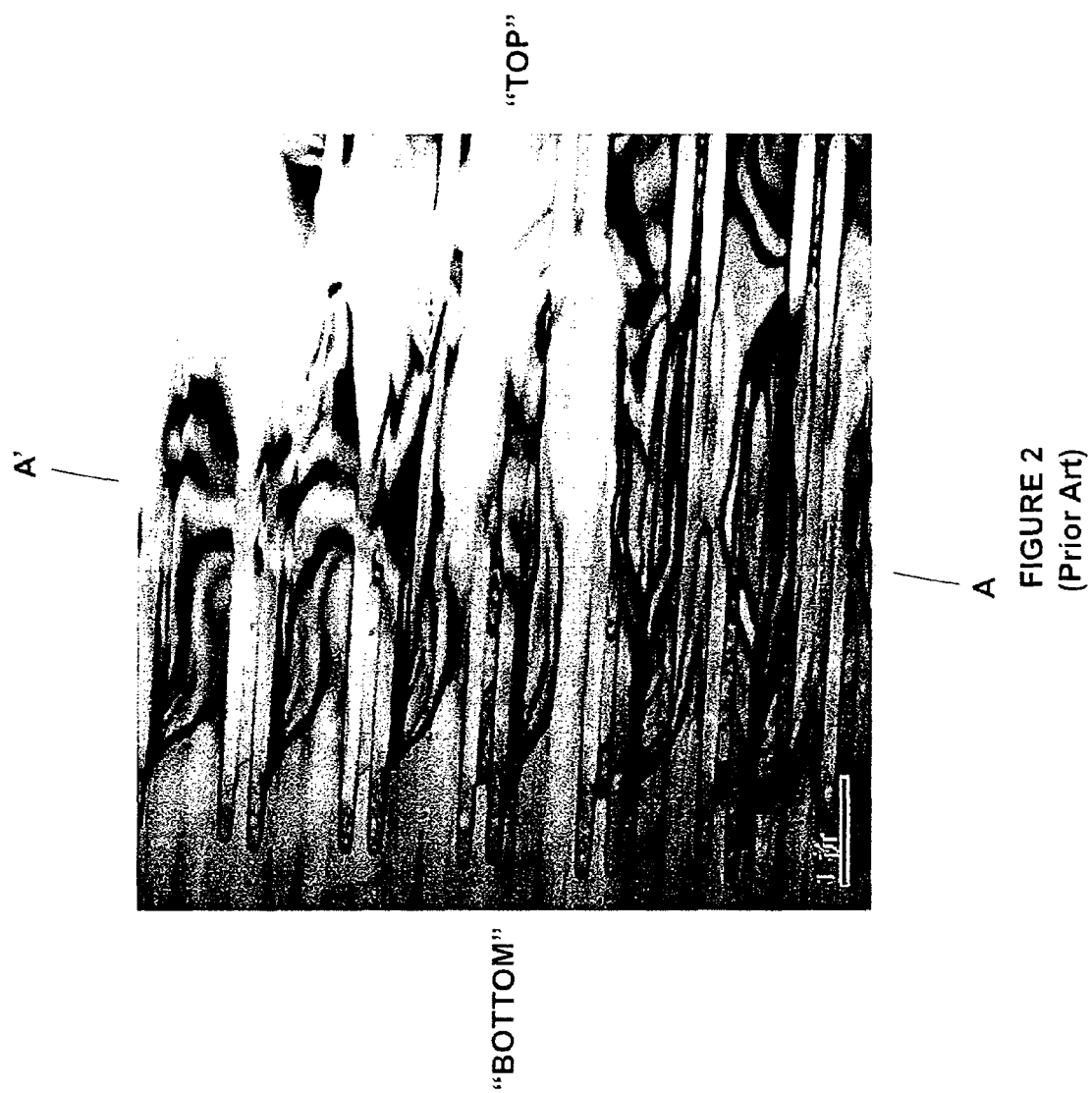
FIGS. 2 and 3 are illustrations of samples prepared using conventional methods.
Figure 3:
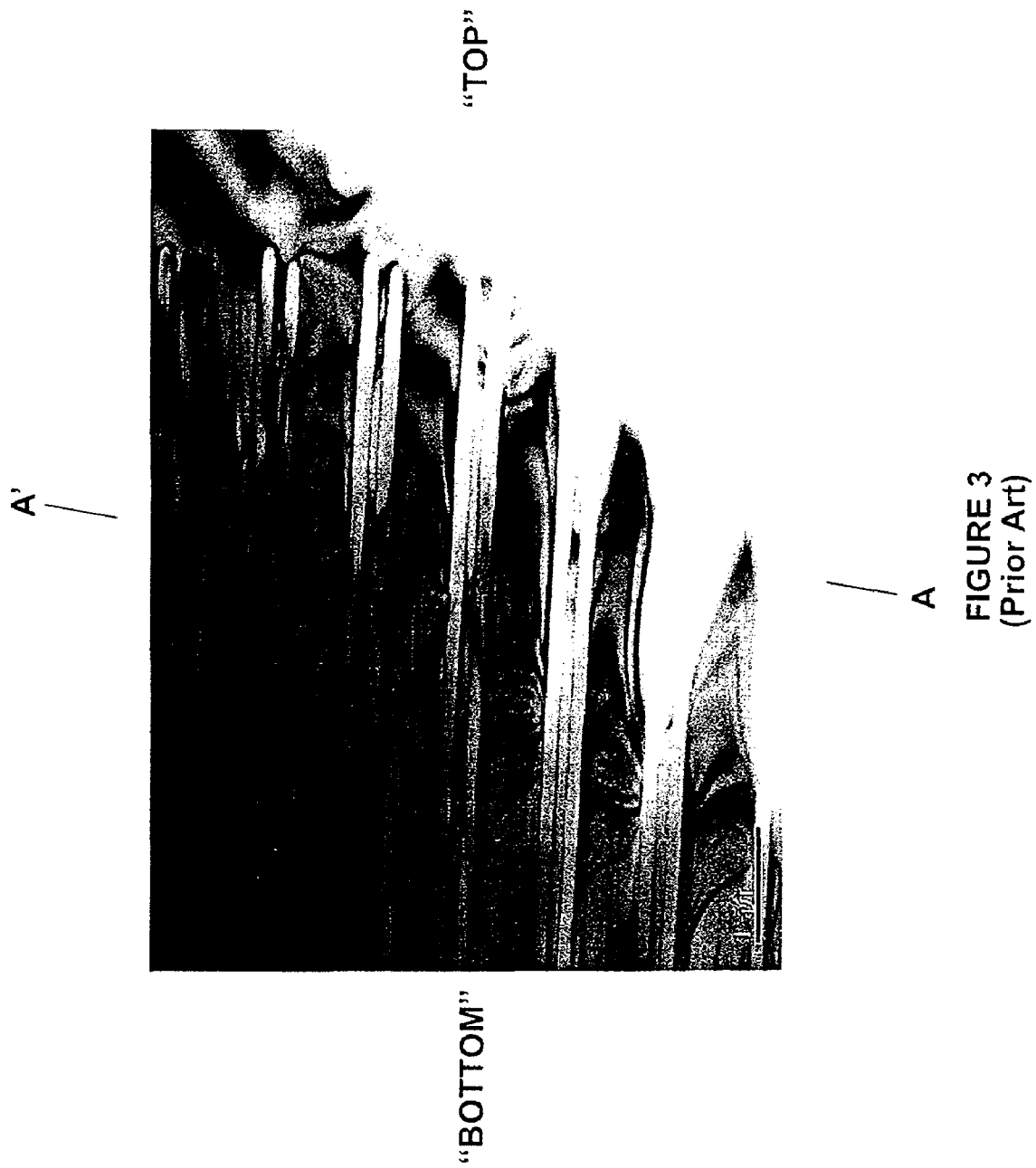

FIGS. 2 and 3 are illustrations of samples prepared using conventional methods. As merely an example, each of the samples have been cut from the top part of the capacitor structure during sample preparation. As shown, each of the samples include a plurality of trench structures. Each of the trench structures become difficult to image near an upper portion (see "TOP") of the trench structure. For cross-referencing purposes, each of the samples includes reference lines A-A', which can be mapped back to the diagram of FIG. 1.

According to a specific embodiment of the present invention, each of the trenches has uniform properties that allows for TEM imaging to occur in an efficient and accurate manner.

According to a specific embodiment, the present method begins sample preparation from each of the elongated side regions of the trench structures. Further details of the present method can be found throughout the present specification and more particularly below.

A method for preparing a sample for TEM analysis for the manufacture of an integrated circuit device according to an embodiment of the present invention may be outlined as follows.

1. Provide an integrated circuit chip. The integrated circuit chip includes a thickness, a width, a length, and at least one elongated structure through a portion of the thickness, while being normal to the width and the length, the elongated structure having a structure width and a structure length that extends through a vertical portion of the thickness;

2. Remove a slice of the integrated circuit chip from a portion of the thickness in a directional manner normal to the structure length, the slice being provided through an entirety of the one elongated structure along the structure length;

3. Cause a portion of a thickness of the slice providing the elongated structure to be of a substantially uniform sample thickness;

4. Capture one or more images through a portion of the slice using a transmission electron microscope;

5. Process the one or more images;

6. Use information derived from the one or more images in the manufacture of integrated circuits; and 7. Perform other steps, as desired.

The above sequence of steps provides a method according to an embodiment of the present invention. As shown, the method uses a combination of steps including a way of preparing an integrated circuit portion for TEM analysis according to an embodiment of the present invention. Other alternatives can also be provided where steps are added, one or more steps are removed, or one or more steps are provided in a different sequence without departing from the scope of the claims herein. Further details of the present invention can be found throughout the present specification and more particularly below.

Figure 4:
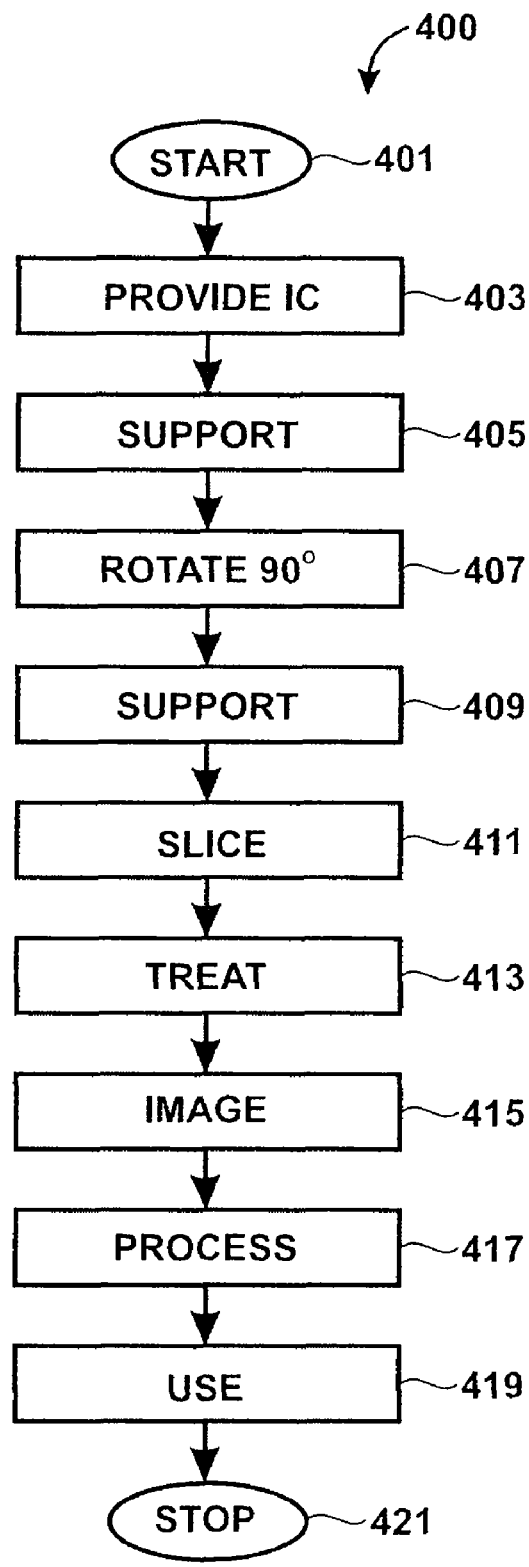
FIG. 4 is a simplified flow diagram illustrating a sample preparation method according to an embodiment of the present invention.

FIG. 4 is a simplified flow diagram 400 illustrating a sample preparation method according to an embodiment of the present invention. This diagram is merely an example, which should not unduly limit the scope of the claims herein. One of ordinary skill in the art would recognize other variations, modifications, and alternatives. In a specific embodiment, the present invention provides a method for analyzing a sample for the manufacture of integrated circuits, e.g., dynamic random access memory device, commonly called, DRAMS. As shown, the method begins with start, step 401. The method also provides (step 403) an integrated circuit chip including a thickness, a width, and a length, which can be supported, step 405. In a specific embodiment, the integrated circuit chip has at least one elongated structure through a portion of the thickness, while being normal to the width and the length. In a specific embodiment, the elongated structure has a structure width and a structure length that extends through a vertical portion of the thickness. Further details of the present structure can be found throughout the present specification and more particularly below.

Figure 5:
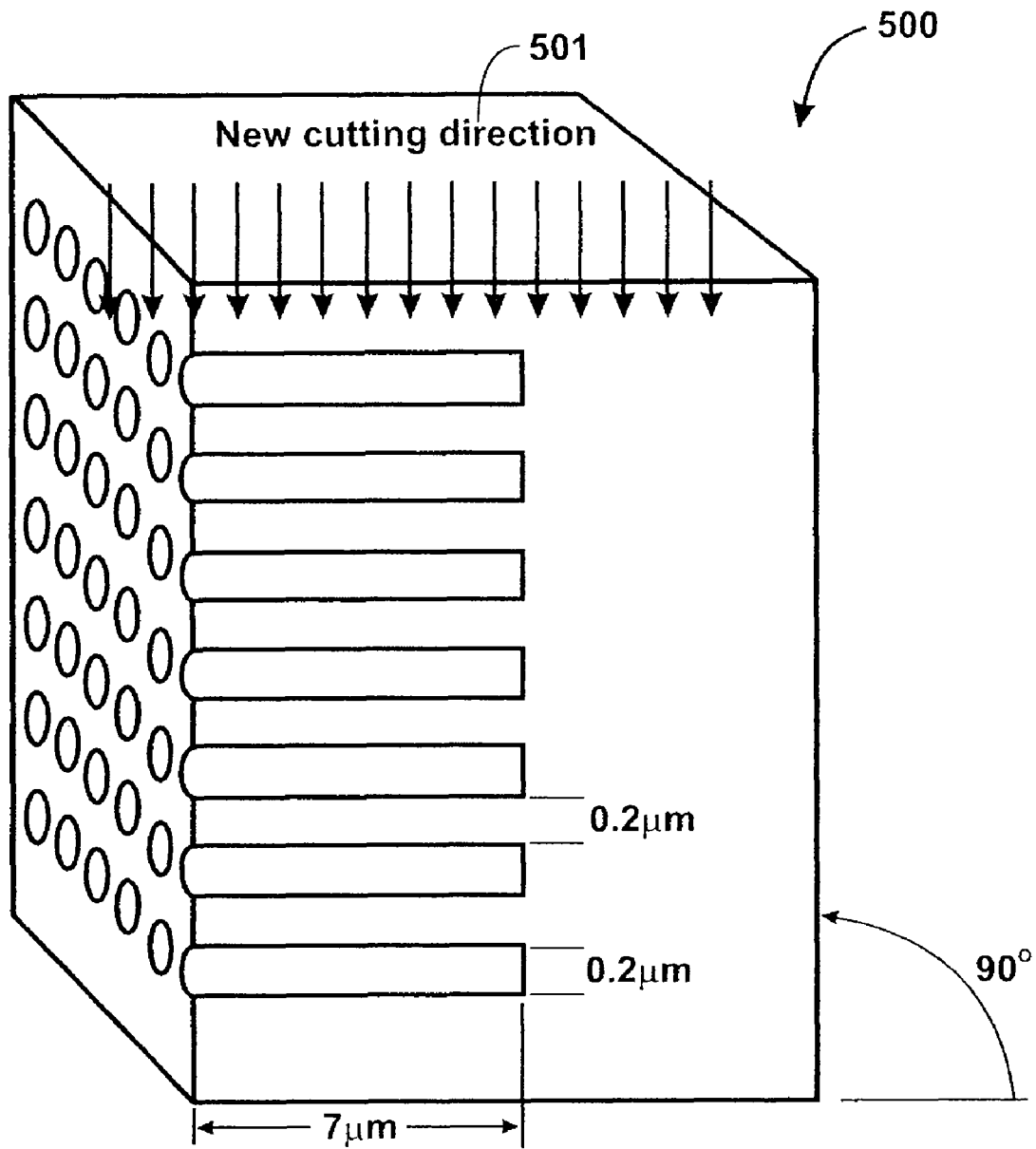
FIG. 5 is a simplified diagram illustrating a method for preparing a sample for TEM analysis according to an embodiment of the present invention.

FIG. 5 is a simplified diagram illustrating a method for preparing a sample for TEM analysis according to an embodiment of the present invention. This diagram is merely an example, which should not unduly limit the scope of the claims herein. One of ordinary skill in the art would recognize other variations, modifications, and alternatives. As shown, the present method includes rotating the integrated circuit structure 90 degrees, such that the thickness of the plurality of elongated structures are normal to the direction of cutting 501, which has been illustrated, See, also FIG. 4, step 407.

Referring back to FIG. 4, the method includes supporting the integrated circuit structure, step 409. The method includes removing a slice (step 411) of the integrated circuit chip from a portion of the thickness in a directional manner normal to the structure length. In a specific embodiment, the slice is provided through an entirety of the one elongated structure along the structure length to cause a portion of a thickness of the slice to be of a substantially uniform sample thickness. In a specific embodiment, the slice is then subjected to one or more treatment steps (step 413), which can be used to enhance a TEM image.

In a specific embodiment, the method also includes capturing one or more images (step 415) through a portion of the slice using a transmission electron microscope. The method also processes (step 417) the captured images to detect any defects, or other information associated with the character of the elongated members. The method uses (step 419) the processed information for the manufacture of integrated circuits including reliability and/or other failure analysis techniques. Of course, there can be other variations, modifications, and alternative. The method can end at stop, step 421. Depending upon the specific embodiment, certain details of the present invention can be found throughout the present specification and more particularly below.

Figure 6:
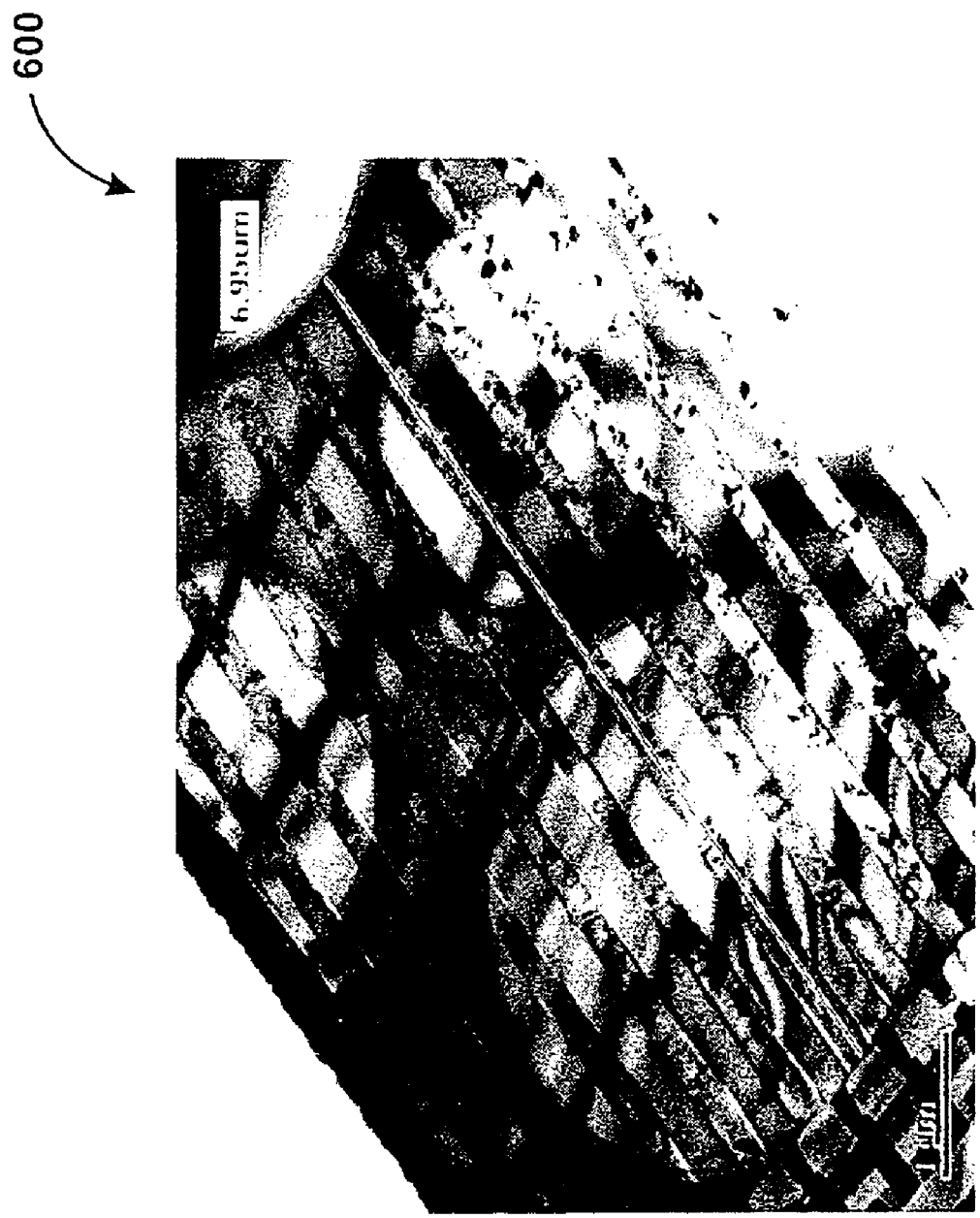
FIGS. 6 and 7 are illustrations of samples prepared using methods according to embodiments of the present invention.
Figure 7:

FIGS. 6 and 7 are illustrations of samples 600, 700 prepared using methods according to embodiments of the present invention. These diagrams are merely examples, which should not unduly limit the scope of the claims herein. One of ordinary skill in the art would recognize other variations, modifications, and alternatives. As shown, the present method provides image 600, which illustrates a plurality of clean elongated structures. As shown in FIG. 7, the method also provides very clear lines, as illustrated. These illustrations are merely examples and have been provided according to methods of the present invention. Of course, there can be other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for analyzing a sample for the manufacture of integrated circuits, the method comprising:
   providing an integrated chip including a thickness, a width, and a length, the integrated chip having at least one elongated structure through a portion of the thickness, while being normal to the width and the length, the elongated structure having a structure width and a structure length, the structure length extending through a vertical portion of the thickness;
   removing a slice of the integrated circuit chip from a portion of the thickness in a directional manner normal to the structure length, the slice being provided through an entirety of the one elongated structure along the structure length to cause a portion of a thickness of the slice providing the elongated structure to be of a substantially uniform sample thickness; and
   capturing one or more images through a portion of the slice using a transmission electron microscope.

2. The method of claim 1 wherein the uniform sample thickness is less than 0.1 microns.

3. The method of claim 1 wherein the elongated structure is a capacitor structure.

4. The method of claim 1 wherein the elongated structure is a stacked via structure.

5. The method of claim 1 wherein the elongated structure is one of a plurality of elongated structures, each of the elongated structures being a parallel to each other.

6. The method of claim 1 wherein the removing is provided by a focused ion beam.

7. The method of claim 1 wherein the elongated structure has a structural length to width ratio of ten or greater.

8. The method of claim 1 wherein the elongated structure comprises a material selected from metal, dielectric, or polysilicon.

9. The method of claim 1 further comprising processing the one or more images captured by the transmission electron microscope.

10. The method of claim 1 further comprising using information derived from the one or more images for the manufacture of integrated circuits.

11. A method for analyzing a sample for the manufacture of integrated circuits, the method comprising:
    providing an integrated chip including a thickness, a width, and a length, the integrated chip having a plurality of elongated structures in a direction of the thickness, while being normal to the width and the length, each of the elongated structures having a structure width and a structure length, the structure length extending through a vertical portion of the thickness;
    removing a slice of the integrated chip from a portion of the thickness in a directional manner normal to each of the elongated structures, the slice being provided through an entirety of each of the elongated structures along each of the structure lengths to cause each of the elongated structures to be of a substantially uniform sample thickness; and
    capturing one or more images through a portion of the slice using a transmission electron microscope.

12. The method of claim 11 wherein the substantially uniform sample thickness is less than 0.1 microns.

13. The method of claim 11 wherein each of the elongated structures is a capacitor structure.

14. The method of claim 11 wherein each of the elongated structures is a stacked via structure.

15. The method of claim 11 wherein each of the elongated structures is in a parallel with each other.

16. The method of claim 11 wherein the removing is provided by a focused ion beam.

17. The method of claim 11 wherein each of the elongated structures has a structure length to width ratio of ten or greater.

18. The method of claim 11 wherein each of the elongated structures comprises a material selected from metal, dielectric, or polysilicon.

19. The method of claim 11 further comprising processing the one or more images captured by the transmission electron microscope.

20. The method of claim 11 further comprising using information derived from the one or more images for the manufacture of integrated circuits.

* * * * *